United States Patent [19]

Evans et al.

[11] Patent Number: 5,417,215
[45] Date of Patent: May 23, 1995

[54] METHOD OF TISSUE CHARACTERIZATION BY ULTRASOUND

[75] Inventors: Steven J. Evans, Great Neck; Scott L. Roth, East Hill; Harold M. Hastings, Garden City, all of N.Y.

[73] Assignees: Long Island Jewish Medical Center; Hofstra University, both of New York, N.Y.

[21] Appl. No.: 191,524

[22] Filed: Feb. 4, 1994

[51] Int. Cl.[6] ............................................. A61B 8/00
[52] U.S. Cl. ............................................. 128/660.06
[58] Field of Search ............... 128/660.01, 660.06, 128/660.07, 661.02–661.09; 73/599, 602

[56] References Cited

U.S. PATENT DOCUMENTS

| | | | |
|---|---|---|---|
| 4,512,195 | 4/1985 | Miwa et al. | 128/660.06 X |
| 4,568,827 | 4/1987 | He et al. | 128/660.06 |
| 4,803,994 | 2/1989 | Burke | 128/660.06 |
| 5,243,987 | 9/1993 | Shiba | 128/661.07 X |

*Primary Examiner*—Francis Jaworski
*Attorney, Agent, or Firm*—Amster, Rothstein & Ebenstein

[57] ABSTRACT

An ultrasound method and apparatus for classification of tissue in a region of interest in a body. The raw ultrasound return data is digitized and processed without the need for human visual analysis of pixel-scale video images. Tissue classification is done by correlation of the relative amount of energy in selected frequency bands of the power spectrum of the returned demodulated ultrasound data to that of known tissue samples.

14 Claims, 6 Drawing Sheets

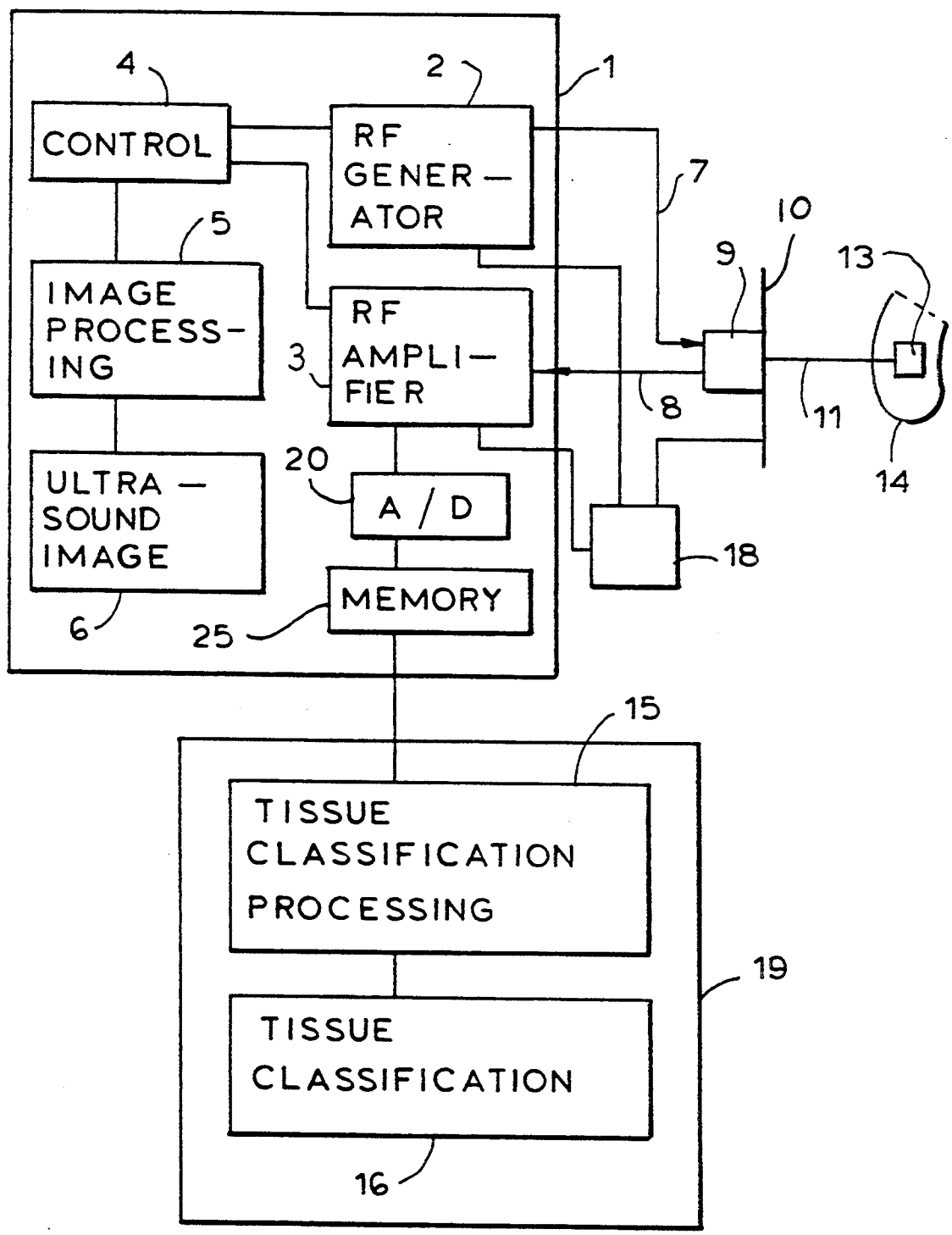
F I G. 1

| SAMPLE NUMBERS | NORMAL A/TOTAL AVG | NORMAL C/TOTAL AVG | SELF-CALIBRATED | | NORMAL C/A RATIO | INFARCT C/A RATIO |
|---|---|---|---|---|---|---|
| | | | INFARCT A/TOTAL AVG | INFARCT C/TOTAL AVG | | |
| A15092 | 0.8917 | 0.0734 | 0.3590 | 0.6298 | 0.0823 | 1.7543 |
| A15093 | 0.9057 | 0.0498 | 0.3272 | 0.6519 | 0.0550 | 1.9924 |
| A16502 | 0.5057 | 0.3566 | 0.3559 | 0.6013 | 0.7052 | 1.6895 |
| A16503 | 0.5849 | 0.3594 | 0.3281 | 0.6183 | 0.6145 | 1.8845 |
| A16504 | 0.8591 | 0.1130 | 0.3536 | 0.6231 | 0.1315 | 1.7622 |
| A16642 | 0.6869 | 0.2725 | 0.3578 | 0.6169 | 0.3967 | 1.7241 |
| A16643 | 0.8755 | 0.0768 | 0.3341 | 0.6425 | 0.0877 | 1.9231 |
| A16644 | 0.8880 | 0.0918 | 0.3214 | 0.6380 | 0.1034 | 1.9851 |
| A16862 | 0.8513 | 0.1016 | 0.3460 | 0.6443 | 0.1193 | 1.8621 |
| A16863 | 0.6624 | 0.3019 | 0.3531 | 0.6206 | 0.4558 | 1.7576 |
| AVG | 0.7711 | 0.1797 | 0.3436 | 0.6287 | 0.2751 | 1.8335 |
| SD | 0.1398 | 0.1201 | 0.0137 | 0.0147 | 0.2329 | 0.1046 |

| SAMPLE NUMBERS | NORMAL A/TOTAL AVG | NORMAL C/TOTAL AVG | NOT SELF-CALIBRATED INFARCT A/TOTAL AVG | INFARCT C/TOTAL AVG | NORMAL C/A RATIO | INFARCT C/A RATIO |
|---|---|---|---|---|---|---|
| A15902 | 0.9230 | 0.0223 | 0.8542 | 0.1338 | 0.0242 | 0.1566 |
| A15093 | 0.5137 | 0.0791 | 0.9410 | 0.0473 | 0.1540 | 0.0503 |
| A16502 | 0.5608 | 0.3512 | 0.6089 | 0.3542 | 0.6262 | 0.5817 |
| A16503 | 0.6440 | 0.3171 | 0.6775 | 0.2902 | 0.4924 | 0.4283 |
| A16504 | 0.9495 | 0.0418 | 0.8583 | 0.1208 | 0.0440 | 0.1407 |
| A16642 | 0.6819 | 0.2878 | 0.6521 | 0.3233 | 0.442 | 0.4958 |
| A16643 | 0.8989 | 0.0714 | 0.8938 | 0.0824 | 0.0794 | 0.0922 |
| A16644 | 0.9372 | 0.0277 | 0.9325 | 0.0239 | 0.0296 | 0.0256 |
| A16862 | 0.8491 | 0.1061 | 0.9413 | 0.0488 | 0.1250 | 0.0518 |
| A16863 | 0.6462 | 0.3280 | 0.6197 | 0.3540 | 0.5076 | 0.5712 |
| AVG | 0.7604 | 0.1633 | 0.7979 | 0.1779 | 0.2504 | 0.2594 |
| SD | 0.1594 | 0.1317 | 0.1336 | 0.1295 | 0.2219 | 0.2190 |

METHOD OF TISSUE CHARACTERIZATION BY ULTRASOUND

FIELD OF THE INVENTION

The invention relates to the medical classification of body tissue as normal or abnormal. More specifically, the invention provides an ultrasound system for determining the type and extent of tissue abnormality in numerical terms which may be evaluated to obtain quantitative, qualitative and visual analysis of the degree and type of abnormality, thus facilitating diagnosis of various diseases.

BACKGROUND OF THE INVENTION

Ultrasound energy is reflected from macroscopic tissue interfaces returning specular reflections, for example, the interface between blood and muscle, and from microscopic components (scatterers) such as cell walls. Both macroscopic interfaces and microscopic scatterers represent acoustic impedance changes which reflect ultrasound energy. Conventional ultrasound images primarily display specular reflections. However, analysis of the characteristics of ultrasound energy reflected from scatterers, as related to tissue type, is preferable for diagnostic purposes.

Constructive and destructive interference among sound waves reflected from various scatterers produces an amplitude modulation of the returned ultrasound signal. Prior art systems can not measure this amplitude modulation on small spatial scales.

Although some of the prior art allows for certain crude morphologic features of tissue to be identified, such as size, thickness, and shape (see, Feigenbaum, H.; *Echocardiography*, 4e, Lea & Febiger (Philadelphia, 1986)), this identification is based on specular reflections. The prior art does not, in most instances, allow for the accurate or adequate characterization of the various scatterers within the tissue in enough detail to make firm diagnoses of the underlying pathology. For example, the only way to tell that heart muscle may have been damaged has been by observing the muscle thickness and shape as the heart beats. Current ultrasound technology does not permit clear distinction between normal and abnormal heart tissue, or allow discrimination of degrees of abnormality. Hence it is difficult to characterize, for example, heart muscle as normal, damaged, or non-living.

Another example of considerable clinical importance consists of the non-invasive classification of breast masses as either benign fibrous tissue or tumors.

The prior art makes use of analog ultrasonic radio frequency data by applying basic analog signal processing techniques to same. These techniques transform the analog signal data into a visual picture for clinical interpretation. Quantification can only be applied to shape, size, and thickness as seen on the visual image. Hence much information about the intrinsic characteristics of the microscopic scatterers within a given tissue or region of tissue is unavailable by the use of the prior art techniques.

Other prior art systems make use of the ultrasonic radio frequency data by applying various mathematical methods to the radio frequency signal to derive a number representing the total amount of reflected ultrasonic energy reaching the transducer (integrated backscatter). In in vitro testing, the integrated backscatter (IB) can be closely related to the reflectance of the tissue and appears to provide a useful discriminator (Miller JG, Perez JE, Sobel BE. "Ultrasonic characterization of myocardium." *Progress In Cardiovascular Disease,* 28:85-110, 1985). However, the IB in clinical situations depends heavily on the amount of power reaching the tissue and the amount of reflected power reaching the transducer. Both factors depend critically upon unknown variables (e.g., attenuation and scatter in the tissue between the transducer and the region of interest). Thus, in order for measurement of IB to be clinically applicable, it requires calibration with an external reference standard (such as a steel plate reflector). Because external calibration cannot be applied to an in vivo situation, many assumptions and estimates concerning tissue absorption must be made, consequently limiting the utility of IB analysis.

U.S. Pat. No. 4,817,015 of Insana et al. provides a method for discriminating between different tissue textures within conventionally processed analog images of the returned ultrasound signals. Insana assumes a single, well-defined spatial texture scale, adds linear and higher order statistical terms, and subtracts an estimated noise curve to locate features within a 4-dimensional feature space. The underlying assumptions built into the Insana system provide many potential sources of error.

Similarly, the system taught in U.S. Pat. No. Re. 33,672 of Miwa provides for analysis of ultrasonic waves of at least three transmitted center frequencies for tissue characterization, but requires assumptions about values of several key variables, including attenuation and the quality of the acoustic coupling at the tissue-transducer interface, both at each of the transmitted center frequencies. In addition, the Miwa system requires the transmission and analysis of a plurality of ultrasound signals having different transmitted center frequencies, wherein the tissue characterization is based upon energy as a function of the centers of the transmitted frequencies and of the ratios among the various energies.

Author, G. Guinta, in "Spectral Noise And Ultrasonic Tissue Characterization", *Frontiers In Medical And Biological Imaging,* Vol. 4, pages 209-217, 1992, teaches a modification of the Miwa method. Guinta considers a broadband ultrasound pulse containing a range of frequencies, and uses the Fourier Transform to separate the return into corresponding components. The transmitted energy at each frequency is determined by applying the same technique to the reflection from a metallic reference scatterer. For each frequency, Guinta obtains a normalized echo signal by dividing the corresponding Fourier energy (coefficient in the power spectrum) in the return from the tissue by that from the reference, a process equivalent to normalizing each of Miwa's returns by the corresponding transmitted power. Guinta's method still requires a reference plate and is thus subject to variations in transducer-tissue coupling and attenuation in the body throughout the range of frequencies used. Efforts to reduce this dependence by reducing the range of frequencies would also limit the amount of data received.

In summary, Guinta uses Fourier techniques to allow transmission and detection of a plurality of transmitted frequencies contained in a single pulse. These methods do not provide for direct measurement of reflectance through self-calibration, and thus in vivo use is still subject to calibration problems inherent in Miwa and in integrated backscatter methods.

In another prior art system, authors Sommer, Joynt, Carroll and Macovski ("Ultrasound characterization of abdominal tissues via digital analysis of backscattered wavefronts", *Radiology*, 141:811-7, 1981) used frequency domain (Fourier) analysis to determine the mean spacing of scatterers in the liver and spleen. Sommer et al. also studied the mean amplitude and variance of the amplitude ("amplitude domain analysis"); however, they did not offer solutions to the problem of assuming values for key variables. The amplitude in the Sommer et al. analysis depends heavily upon the variables of acoustic efficiency of the transducer and tissue absorption just as in IB analysis.

It is, therefore, an objective of the invention to provide an improved ultrasound tissue characterization system and method for quantifying and classifying the direct ultrasound data.

It is a further objective of the invention to provide an ultrasound tissue characterization system which requires neither an external reference point nor assumptions about crucial variables.

SUMMARY OF THE INVENTION

These and other objectives are realized by the present system wherein measurement and analysis of spectral (e.g., Fourier) characteristics of the amplitude modulation of a returned ultrasound signal enables determination of the types and relationships among scatterers within a region of tissue. The relative amount of amplitude modulation as a function of spatial scale is readily determined without external calibration or separate assumptions or estimates regarding tissue absorption, reflectance, and attenuation. The novel method then produces numerical discriminants between normal and abnormal tissue, and can further be applied to identify varying degrees of abnormality.

BRIEF DESCRIPTION OF THE DRAWINGS

The invention will now be detailed with specific reference to the drawings wherein:

FIG. 1 is an overview of the inventive ultrasound system.

FIGS. 5A and 5B provides a table of representative ultrasound tissue characterization results obtained with and without utilizing a key step in the present invention, respectively.

DETAILED DESCRIPTION OF THE PREFERRED EMBODIMENT

Figure 2:
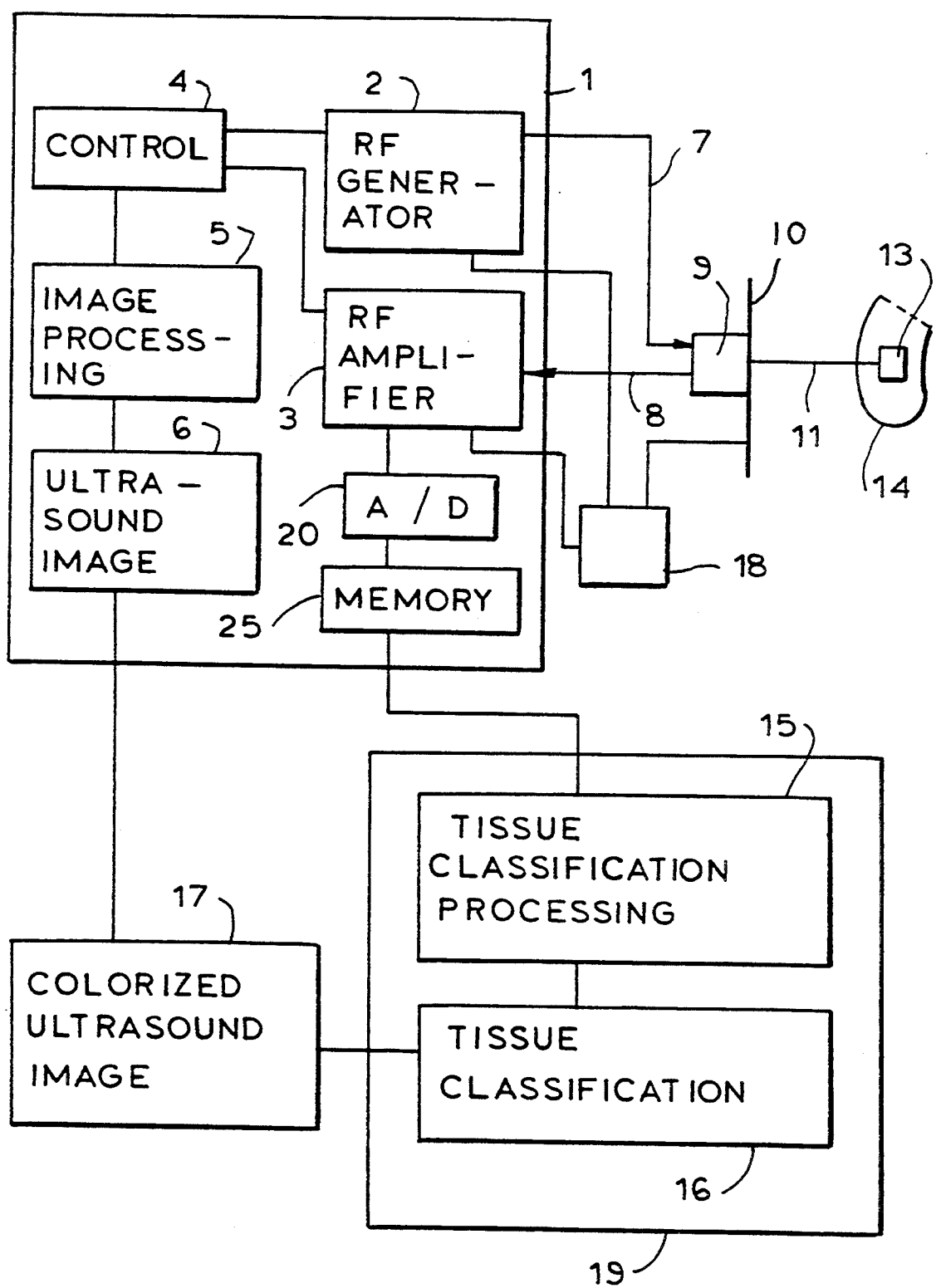
FIG. 2 is an illustration of the inventive ultrasound system additionally equipped with a colorized ultrasound imager.

Referring to FIG. 1, a transducer, 9, is placed on or inside the body of the patient, 10, and connected to a standard ultrasound machine, 1. The processor, 19, of the present invention classifies tissue based on analysis of the raw ultrasound return from the RF amplifier, 3, of the ultrasound machine, 1, rather than by pixel scale visual characterization of a video image at image 6, which necessarily cannot reproduce information in sub-pixel tissue increments. Conventional ultrasound images are produced from ultrasound energy reflected by macroscopic interfaces between tissues of differing acoustic impedance (specular reflection). As discussed above, ultrasound energy is additionally reflected from impedance variations among microscopic components within a region of tissue, the components being referred to as scatterers. It is to be noted that the larger-scale macroscopic interfaces observed in conventional ultrasound images also serve as scatterers. However, in accordance with usage in the field of medical ultrasound, we will apply the term "scatterers" exclusively to smaller "microscopic" impedance changes within regions of tissue. Constructive and destructive interference among sound waves reflected from various scatterers produces an amplitude modulation of the returned ultrasound signal. The present system and method measures the spectral characteristics of this amplitude modulation to determine the spatial relationships amongst scatterers and thus the classification of the tissue within a region of tissue.

With reference to FIG. 1, the RF generator, 2, in the ultrasound machine, 1, sends an RF signal, 7, to the transducer, 9. The transducer emits an ultrasound pulse which travels along scan line 11 into the tissue of interest, 14, in the body, 10. The signal generated $y_g(t)$ by the RF generator is represented by the formula:

$$y_g(t) = \begin{cases} y_0 \cos 2\pi f t & -\Delta t/2 \leq t \leq \Delta t/2 \\ 0 & \text{otherwise} \end{cases}$$

where $y_g$ is expressed in volts .or millivolts, f(center frequency) is expressed in MHz, t(time) is expressed in microseconds and $\Delta t$ represents the pulse duration in microseconds. The emitted ultrasound pulse is necessarily attenuated before it reaches the region of interest, 13, within the tissue 14, the effect of which will be detailed further herein.

Multiple sites can be successively examined within the region of interest, 13, with scatterers encountered at each site, which scatterers reflect and modulate the amplitude of the ultrasound signal. The reflected ultrasound signal from each site returns along the same scan line, 11, towards the transducer, 9. What is received at transducer 9 as the ultrasound return, $Y_r$, is the attenuated reflected ultrasound signal as shown by the formula:

$$y_r(t) = \int du\, y_g(t-u)(e_o a_o(u) e_i a_i(u))\, R(u)$$

where $e_o$ represents the output transducer efficiency from the RF generator to the ultrasound machine, $e_i$ represents the transducer efficiency from the ultrasound machine returning to the RF amplifier, $a_o$ represents the attenuation in the outgoing direction, and $a_i$ represents the attenuation in the incoming direction. All of the foregoing variables, $e_o$, $e_i$, $a_o(u)$, $a_i(u)$ are variables whose values have, in the past, been estimated or assumed. For purposes of the present implementation, the product of these variables will be expressed as unknown collective value $E(u)$. $R(u)$ in the foregoing formula is the reflectivity of scatterers or interfaces at a depth of $(v/2)u$ microns, where v is the average speed of sound along the scan line in meters per second or, the equivalent, microns per microsecond.

Transducer 9 converts the attenuated reflected ultrasound signal to RF signal 8 which is then fed from the transducer, 9, to the RF amplifier, 3. In the prior art, this RF signal would be used to produce an image, at 6, for visual analysis. In the preferred embodiment, however, the output from RF amplifier 3, that is the amplified RF signal of the ultrasound return, is fed to an analog-to-digital converter, 20. The analog-to-digital converter yields a digitized, sampled, amplified ultrasound return, which can be stored at computer memory, 25 or immediately provided for processing at processor 19. As successive waveforms arrive at the computer memory, they can be demodulated and/or averaged with stored preceding waveform(s) from the same tissue site or input for successive processing at processor 19. Moreover, digitizing, demodulating, averaging and further processing can, as will be apparent to one having ordinary skill in the art, be conducted by a single "processor means" adapted to perform the successive "steps".

An optional gating circuit, 18, may be attached to the device at one or more points in the overall system (e.g., to the RF generator, 2, or to the RF amplifier, 3) and the patient, 10, to allow for collection of data at specific times, such as multiple collections serially at a fixed point during one or multiple cardiac cycles or respiration iterations.

Figure 3:
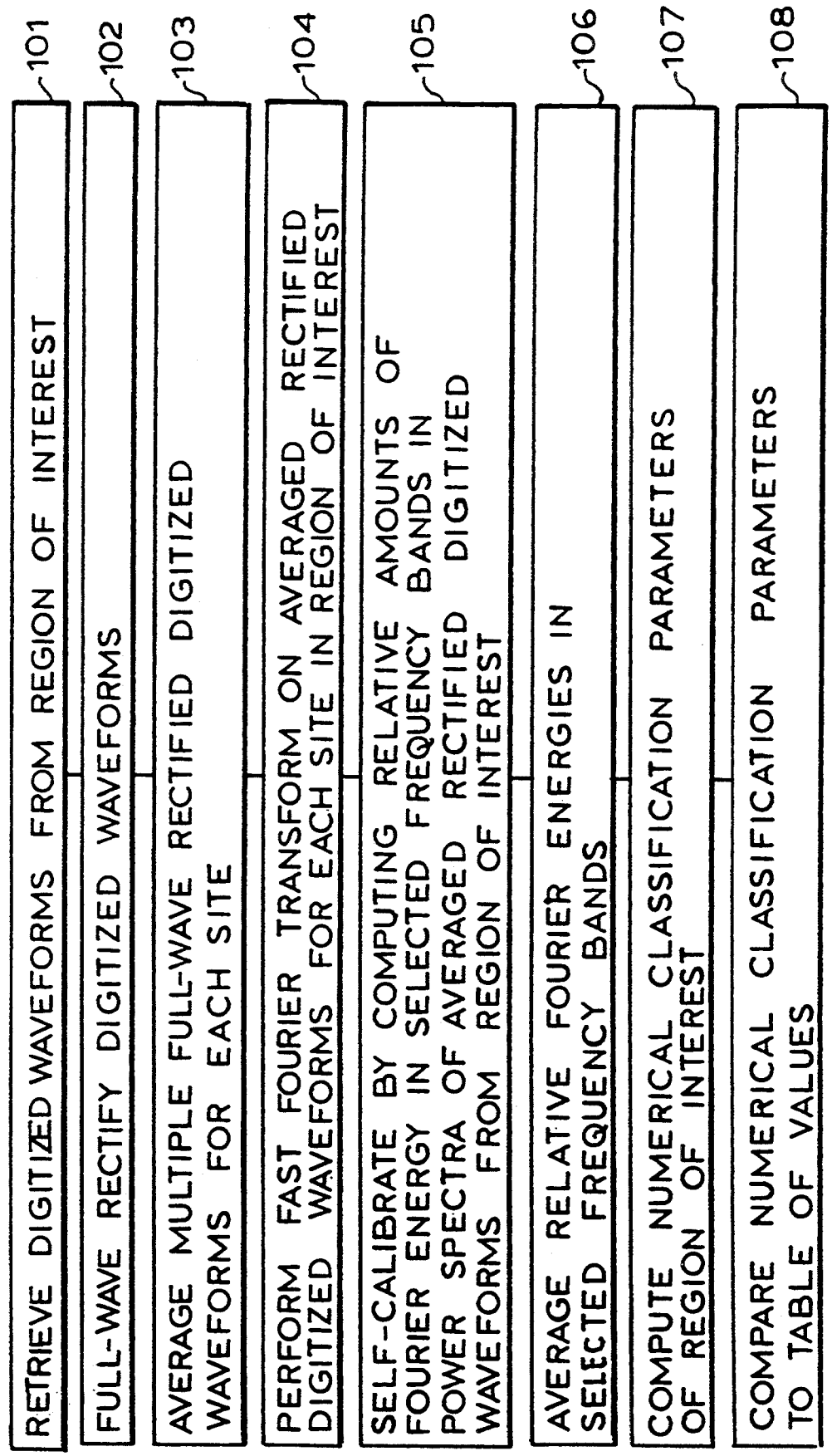
FIG. 3 provides the process flow utilized in processing the ultrasound data and characterizing the tissue in accordance with the present invention.

The processing of the ultrasound return data from each region of interest, 13, will be described with reference to the process flow illustrated in FIG. 3. The digitized waveforms, which have arrived in computer memory 25 and been stored, are retrieved at block 101, in the format ($\{y_r(i,j,t)\}$). For each region of interest, there are many sites indexed by "$i=1 \ldots i_{max}$". Within each site, there are many separate digitized waveforms indexed by "$j=1 \ldots j_{max}$". Successive time steps in each waveform are indexed by "$t=1 \ldots t_{max}$". For any given $i_o$ and $j_o$ $\{Yr(i_o,j_o,t)\}$ represents the $j_o$th digitized waveform from site $i_o$. As noted above, the waveforms may be provided directly from converter 20 to processor 19 in the same format.

It is to be noted that, prior to step 101, an optional windowing step can be performed, in accordance with known prior art techniques, in order to reduce the effects of non-periodicity in the ultrasound return.

For all sites in each region of interest, 13 in FIG. 1, the corresponding digitized waveforms are full-wave rectified or otherwise demodulated, at 102, so as to recover the amplitude modulation in the digitized waveform due to constructive and destructive interference among sound waves reflected from various scatterers. Moreover, in order to reduce noise, as noted above, the multiple, rectified, digitized waveforms indexed by ($j=1 \ldots j_{max}$) from each site are ideally averaged at 103, yielding averaged, rectified, digitized waveforms. These averaged, rectified, waveforms are then indexed by site ($i=1 \ldots i_{max}$). Averaging reduces the effects of random fluctuations in the amplitude modulation of the transmitted waveform by scatterers, which fluctuations might arise within the system, at acoustic interfaces, or in the body, for example as a result of small-scale (e.g., 1 mm) motions. Averaging also reduces the effects of any other noise. Thus, the actual averaged, rectified, digitized received waveform is closer to its theoretical value than separate components (rectified, digitized received waveforms) of the average, and is therefore detailed in the description of the preferred embodiments.

A plurality of averaged, rectified, digitized waveforms may be obtained from a plurality of sites in each region of interest, 13. In addition, a plurality of regions of interest, 13, from the tissue of interest may be scanned, automatically or under operator control. The processing of the waveforms from each site or region, 13, may be done at any time after the waveforms from that site or region have been obtained.

The device next determines the energy in each of a plurality of selected frequency bands of the power spectrum of the digitized pulses. For this embodiment, at step 104, a Fourier analysis is performed on the averaged, rectified, digitized waveforms from each site in the region of interest yielding the energy amplitudes and phases of the various Fourier components.

Note that applying the Fourier transform after our inventive step of full-wave rectification or equivalent demodulation yields a Fourier decomposition of the amplitude modulation of the ultrasound return due to constructive and destructive interference; whereas applying the transform to the raw return is equivalent to the use of a corresponding range of transmitted center frequencies.

After Fourier analysis is performed and the power spectrum (i.e., the sum of squares of the amplitudes of the corresponding Fourier coefficients) obtained, the inventive system computes relative amounts of energy for the selected frequency bands. Step 105 takes ratios of the power spectra associated with two or more selected frequency bands, in this embodiment, relative Fourier energies. The relative energies in selected frequency bands correspond to fluctuations in the amplitude of the averaged, rectified, digitized ultrasound returns from the region of interest on corresponding spatial scales. In one implementation of the invention, the energy in each selected frequency band (e.g., low, medium and high frequency) is compared to the total energy in all bands, yielding a relative distribution of energy as a function of the frequency of the Fourier components.

Step 105 is referred to as the self-calibration step. In computing the relative amounts of energy, the unknown variable, $E^2$ representing the transducer efficiencies and attenuation in the outgoing and incoming directions, cancels out of the ratio, as illustrated in the formulae set forth below. There is, accordingly, no need to calibrate the system based upon estimated attenuation and efficiency values since these variables do not affect the results of the tissue characterization process. Characterization of the tissue can, therefore, be conducted directly on the "raw" ultrasound data using the Fourier components in the averaged, rectified, digitized waveform which represent spatially periodic components in the amplitude modulation of the RF signal. The spatially periodic components correspond to the ultrasound return variations, attributable solely to the reflectivity and geometry of the scatterers as an indicator of the composition of the tissue. The foregoing determination of the energy in any given frequency band can be done by a microprocessor, or can be performed by applying a suitable time-domain filter to the averaged, rectified, digitized waveform, followed by integrating the square of the output of the filter. As will be discussed further herein, the ratio of any homogeneous functional of the returned waveforms may be employed with the self-calibration result of the unknown variables cancelling out of the ratio, leaving the relative energy values for use in the tissue characterization.

Averaging of the relative Fourier energies in selected frequency bands, as performed on the relative Fourier energies at 106, may be done in order to further reduce the effects of random fluctuations or variations among sites in a suitable small region of interest, that is, a region small enough to reasonably classify or categorize.

Thereafter, numerical classification parameters are computed for the given region of interest, at step 107. One method for computing these parameters finds the average relative amounts of energy in the selected frequency bands in the power spectra of the averaged, rectified, digitized ultrasound returns from the regions of interest. Data from this calculation obtained in step 107 is then compared to a table of values, at 108, to allow tissue classification. This will allow a more accurate and precise diagnosis of the underlying anatomic and physiologic pathology.

Illustrating the above process steps with the relevant formulae, we observe the following:

$$y_g(t) = \begin{cases} y_o \cos 2\pi f t & -\Delta t/2 \leq t \leq \Delta t/2 \\ 0 & \text{otherwise} \end{cases}$$

Then, theoretically, $$y_r(t) = \int du\, y_g(t-u)(e_o a_o(u) e_i a_i(u)) R(u) = \int du\, y_g(t-u) R(u)$$

where $R(u)$ is the reflectivity of scatterers at depth $(v/2)u$ microns and $j = 1 \ldots j_{max}$ $E(u)$ which is $e_o a_o(u) e_i a_o(u)$, represents the overall efficiency of the system at depth $(v/2)u$ microns, and $v$ is the average speed of sound in tissue along the scan line, in meters/second or equivalently microns/microsecond. In tissue, $v$ is typically about 1540 meters/second.

The digitized waveform is $$y(k) = \int du\, y_g(t_k - u) E(u) R(u), \quad k = 1 \ldots k_{max}$$

where $t_1, t_2, \ldots, t_{k\,max}$ are equally spaced discrete times. The time step $\Delta t = t_{k+1} - t_k$ is the inverse of the sampling frequency. In our case, for example, with a representative sampling frequency of 50 MHz, $\Delta t$ will equal 0.02 microsecond.

In the preferred implementation, the sampling frequency must be large compared with the highest frequency present in the transmitted ultrasound signal. The Nyquist limit requires at least a factor of 2, with larger factors being preferable. If such sampling is not possible, an alternate implementation can be used, in which the rectification step is performed directly on the ultrasound waveform in analog circuitry (e.g., with a standard precision full-wave rectifier circuit), followed by a low-pass filter with a cutoff frequency which is small compared with the sampling frequency. As above, the Nyquist limit requires at least a factor of 2 between the sampling frequency and the cutoff frequency, with larger factors being preferable.

A plurality of digitized waveforms is obtained from each of a plurality of sites within a region of interest. Each site is on one scan line; however, a given scan line may be on several sites. In this case, the range of values of $k$ will go beyond $1 \ldots k_{max}$ to a range $1 \ldots K$, where $y_g$ is expressed in volts or millivolts, $f_c$ (center frequency) is expressed in MHz, $t$(time) is expressed in microseconds, and $\Delta t$ represents the pulse duration, again in microseconds. The $j_o$th digitized waveform from the $i_o$th site may still be denoted $$\{y(i_o, j_o, k)) | k = 1 \ldots k_{max}\},$$

following windowing. (selecting a subset of $k_{max}$ consecutive values of $y(i_o, j_o, k)$, $k = k_o + 1 \ldots k_o + k_{max}$ from the range $1 \ldots K$) and reindexing so that the reindexed values of $k$ cover the range $1 \ldots k_{max}$.

One may also optionally apply any of a variety of additional windowing techniques (Hamming, Hanning, etc.) which smoothly taper $y(i_o, j_o, k)$ to 0 as $k$ approaches either of the ends, 1 or $k_{max}$. This reduces the effects of non-periodicity in the ultrasound return.

Finally, the Fast Fourier Transform algorithm requires that $k_{max}$ be a power of 2 for most efficient implementation of the Fourier transform. We used $k_{max} = 256$ for our in vitro testing. Alternatively, if $k_{max}$ is not a power of 2, one may apply the Hamming, Hanning, or a similar window which tapers the signal smoothly to 0 at $k = 1$ and $k = k_{max}$, and then follows the signal with enough 0's to obtain a signal of length the next power of 2.

More generally, the set of all waveforms from all sites is denoted as follows:

$$\{y(i, j, k) | i = 1 \ldots i_{max}, j = 1 \ldots j_{max}, k = 1 \ldots k_{max}\},$$

where sites are indexed by $i = 1 \ldots i_{max}$ and the waveforms within each site are indexed by $j = 1 \ldots j_{max}$.

The $j_o$th rectified, digitized waveform from the $i_o$th site is denoted:

$$\{abs)y(i_o, j_o, k)) | k = 1 \ldots k_{max}\},$$

and has the following theoretical value:

$$abs(y(i_o, j_o, k)) = abs(\int du\, y_g(t_k - u) E(u) R(u)), \quad k = 1 \ldots k_{max}\},$$

Although $E(u)$ may vary significantly between adjacent lines as they pass through different types of tissue, it varies only slowly (compared with the size of a site) along any single line. For example, our in vitro testing used averaged, rectified, digitized waveforms $$\}z(i_o, k) | k = 1 \ldots k_{max}\}$$

consisting of $k_{max}$ or 256 points at a sampling rate of 50 MHz. This corresponds to a total time interval of 5.12 microseconds in the site, and, assuming an average velocity of sound of 1540 m/second = 1.54 mm/microsecond in tissue, a depth of approximately 4 mm for the site. In addition, for our transmitted ultrasound pulse of 1.5 cycles at 7.5 MHz, $y_g(s) = 0$ outside a time interval of half-width 0.1 microsecond centered about time 0. Thus each value $z(i_o, k)$ of an averaged, rectified, digitized waveform corresponds to a spatial window having a half width of approximately 77 microns. Also all points in a site are within 2 mm of the center of the site along a single scan line, and all returns come from a slightly larger spatial window of half-width approximately 2.1 mm.

Following the theme of this example, in general, all points in a site come from a very small neighborhood of the center of that site, and all returns come from a slightly larger neighborhood of that center. For each site, indexed by $i_o$, we may therefore replace $E(u)$ in the integral above by its average value within that site, denoted $E_{avg}(i_o)$, obtaining the simpler expression which closely approximates the theoretical value of $abs(y(i_o, j_o, k))$, namely:

$E_{avg}(i_o)$ abs($\int du\ y_g(t_k-u)R(u)$), $k=1\ldots k_{max}$.

Replacing the variable $u$ by $s=u-t_k$ yields $E_{avg}(i_o)$ abs($\int ds\ y_g(t_k-u)R(u))=E_{avg}(i_o)$ abs($\int ds\ y_g(-s)\ R(t_k+s)$), $k=1\ldots k_{max}$.

Recall that $$y_g(t) = \begin{cases} y_o \cos 2\pi ft & -\Delta t/2 \leq t \leq \Delta t/2 \\ 0 & \text{otherwise} \end{cases}$$

and hence $y_g(-s)$ is zero outside the small neighborhood of 0, $\{s\,|\,-\Delta t/2 \leq s \leq \Delta t/2\}$, and has an amplitude $y_o$ within that neighborhood. We therefore divide by factors corresponding to the amplitude and duration of the transmitted ultrasound pulse and define the effective reflectance at depth $(v/2)t_k$ as:

$R_{eff}(t_k)=(1/(y_o\,\Delta t))$ abs($\int ds\ y_g(-s)\ R(t_k+s)$).

Note in particular that $R_{eff}(t_k)$ is independent of the overall efficiency of the systems $E(u)$. The approximate theoretical value of the rectified, digitized waveform abs$(y(i_o, j_o, k))=$abs $(\int ds\ y_g(-s)\ R(t_k+s))$ can now be written as:

$E_{avg}(i_o)y_o\Delta t\ R_{eff}(t_k)$.

Applying the FFT to the averaged, optionally windowed, digitized rectified waveforms yields:

FFT$\{z(i_o,k)\,|\,\}(f)=$FFT$\{[E_{avg}(i_o)y_o\Delta t]R_{eff}(t_k)\}(f)$.

Since the FFT is linear, we can move the factor $[E_{avg}(i_o)y_o\Delta t]$ outside the FFT obtaining:

FFT$\{z(i_o,k)\,|\,\}(f)=[E_{avg}(i_o)y_o\Delta t]$FFT$\{R_{eff}(t_k)\}(f)$.

Moreover, the power spectrum associated with a given frequency band is just the sum of squares of amplitudes of the corresponding Fourier coefficient, that is $\Sigma_{f\,in\,frequency\,band}$
$\|\,$FFT$\{z(i_o,k)\,|\,\}(f)\,\|^2=[E_{avg}(i_o)y_o\Delta t]^2\times\Sigma_{f\,in\,frequency\,band}\,\|\,$FFT$\{R_{eff}(t_k)\}(f)\,\|^2$.

The ratio of the power spectra associated with two frequency bands, 1 and 2 is given by:

$[\Sigma_{f\,in\,band\,1}\,\|\,$FFT$\{z(i_o,k)|\}(f)\,\|^2]/$ $[\Sigma_{f\,in\,band\,2}\,\|\,$FFT$\{z(i_o,k)|\}(f)\,\|^2]$, and reduces to the ratio:

$[\Sigma_{f\,in\,band\,1}\,\|\,$FFT$\{R_{eff}(t_k)\}(f)\,\|^2]/$ $[\Sigma_{f\,in\,band\,2}\,\|\,$FFT$\{R_{eff}(t_k)\}(f)\,\|^2]$.

The unknown factors $E^2$ have cancelled out. This is the self-calibration of step 105. Note that a self-calibration applies to any ratio of homogeneous functionals (e.g., linear, quadratic, etc.) of the returned waveforms of the same degree $r$, where a functional $T$ from the set $\{w\}$ of waveforms to the set of real real-numbers is called "homogeneous of degree $r$" if for some fixed integer $r$, and any real number $c$, $T(cw)=c^rT(w)$.

For example, the functionals $\Sigma_{f\,in\,band\,1}\,\|\,$FFT$\{\,\}(f)\,\|^2$ and $\Sigma_{f\,in\,band\,2}\,\|\,$FFT$\{\,\}(f)\,\|^2$ are both homogeneous of degree 2.

Thus, self-calibration can be combined with wavelet or similar analysis, just as with the presently described Fourier analysis. As will be apparent to one having skill in the art, self-calibration can also be applied in one, two, three or multi-dimensional space to the results of wavelet or similar variation of analysis, wherein the cancellation formula of the above-referenced equations may apply to any ratio of homogeneous functional of the returned waveform(s).

As noted above, the numerical classification parameters produced for the tissue in the region of interest may be compared to a table of values for related tissue. The table of values, stored in a register or other computer memory location for automatic accessing and comparison, or stored elsewhere for off-line comparison of the numerical classifications, comprises data which has been gathered and correlated for the category of tissue with the express purpose of creating a control data base for comparison. Values for known normal tissue composition, known tissue having abnormalities of the type traditionally encountered and of known degree (e.g., malignant tissue, reparable damaged heart tissue, irreparable damaged heart tissue), and known non-tissue components traditionally associated with the type of tissue (e.g., plaque in coronary arteries), are generated and stored, along with the known diagnosis to which the value of each numerical classification parameter is correlated. Upon comparison of the numerical values for the tissue being tested to the known values, therefore, characterization of the tested tissue can be done utilizing the diagnostic results as correlated to the known values. The table of known values may include values determined during earlier testing of the same tissue in the same patient, during testing of different tissue in that patient, during testing of the same category of tissue in many patients, etc.

After this cycle has been completed, or at any other time, the ultrasonic transducer may then be moved, automatically or under operator control, to scan another area, and the process begun again. In this way, quantification and more accurate diagnosis of disease may be achieved by processing successive areas of tissue within the same organ and/or different organs.

Although the processing steps, and the processor means adapted to perform said steps, are described as independent features, it is clear that one skilled in the art can implement the inventive process in a variety of manners, including the use of circuit components capable of implementing two or more of the separately-recited steps in a single function. Moreover, a single processor means, as illustrated at 19 in FIGS. 1 and 2, may be separated into components without changing the effective functionality, which functionality is recited by the process claims to encompass reasonable equivalents thereto.

The potential spatial resolution for tissue characterization in accordance with the present invention is significantly better than the resolution realized by the prior art systems which relied upon analog image processing. A pulse of c cycles of a signal with a center frequency $f_c$ MHz has a duration of $c/f_c$ microseconds. There is some amount of uncertainty, on the order of $c/f_c$ microseconds, the duration of the round-trip of the ultrasound energy from the transducer to scatterers in a site in a region of interest and back. Assuming the speed of sound in tissue is approximately 1540 meters per second (or 0.154 cm/microsecond), the calculated temporal uncertainty corresponds to a spatial uncertainty of 0.077 $c/f_c$ cm. With the number of cycles typically in the range of 1.5 and a realistic center frequency of 7.5 MHz, then fluctuations in the distribution of scatterers can be measured on spatial scales as small as 150 microns. Such a potential spatial resolution is unattainable under the previously available technology.

A further advantage of the present invention is realized due to the fact that the numerical analysis for tissue characterization is performed independent of the value of the center frequency of the transmitted ultrasound signal. The transmitted center frequency can then be chosen to optimize penetration and spatial resolution of the particular tissue and medium. In contrast, many prior art systems require the use of specific center frequencies, at least some of which may be less than optimal for a given procedure and/or tissue.

Moreover, noise reduction through averaging, and elimination of unknown parameters relating to efficiency and attenuation through self-calibration, together facilitate the analysis of very weak return signals. This allows for the use of higher transmitted center frequencies than the prior art.

Figure 4:
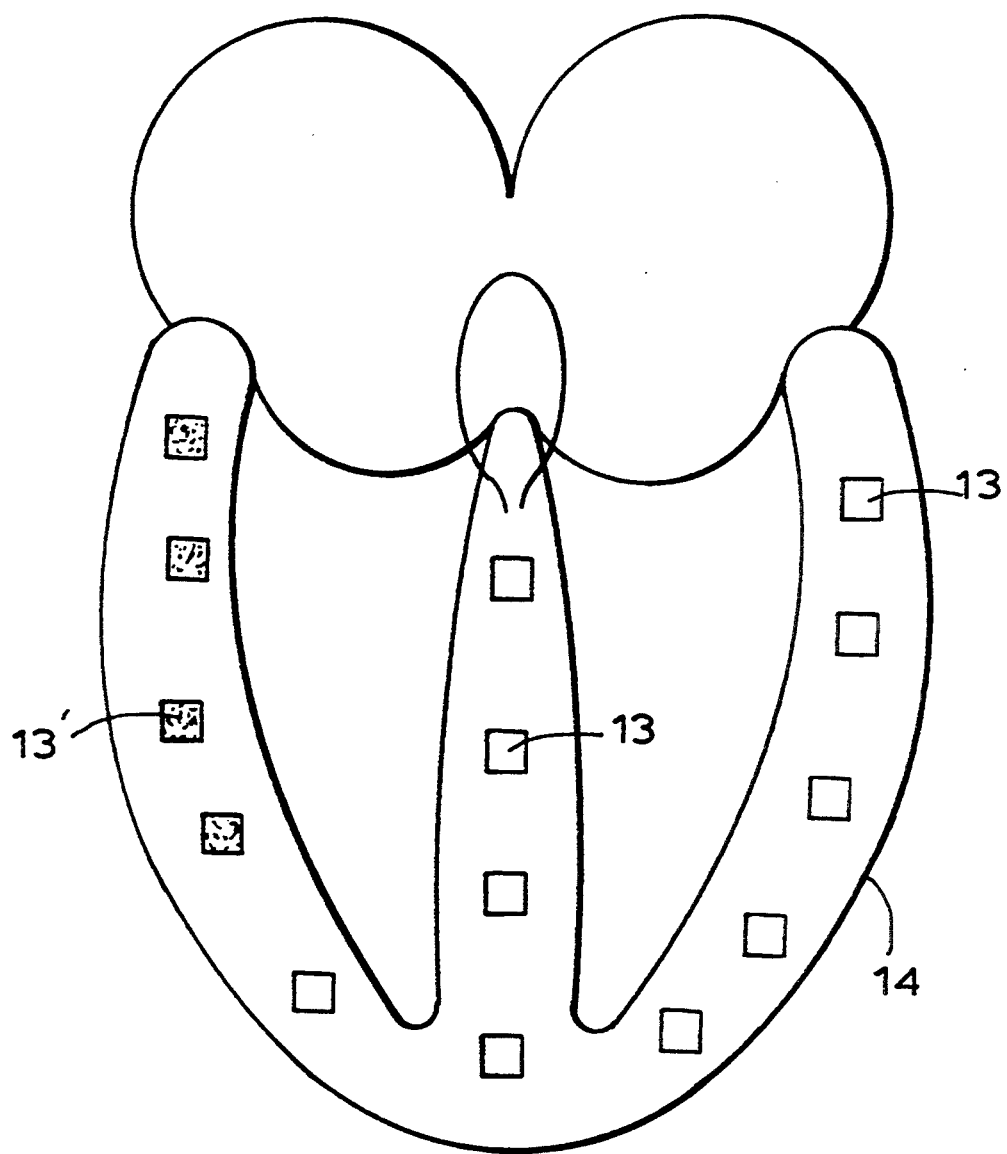
FIG. 4 provides a schematic illustration of heart muscle having regions of normal and abnormal tissue.

Referring to FIG. 2, a conventional ultrasound machine generates an image, 6, from the amplitude of reflected energy from the region corresponding to each pixel using conventional analog image processing, 5. The amplitude is converted to a grey scale value for the relevant pixel using a logarithmic compression algorithm. These conventional means and methods of generating an ultrasound image, 6, can be combined with the present tissue classifying means and methods to obtain a colorized image, 17, (illustrated in FIG. 4) of a region of tissue, instead of the conventional ultrasound image described above. In the colorized image, 17, the color of each sub-area or pixel would correspond to its classification as normal or abnormal. Gradations of color may also be used to represent indeterminate pixels, or intermediate states between "most likely normal" and "most likely abnormal." The classification can also be restricted to a region of tissue, corresponding for example to part of an organ, such as the heart wall, which has been selected using a conventional ultrasound image, 6, obtained from the same machine. FIG. 4 illustrates a schematic of sites of heart tissue having both normal (13) and abnormal (13') tissue regions.

The tables located in FIGS. 5A and 5B provide an illustration of the effectiveness of the present method of tissue characterization. The tables have been generated for the same heart tissue samples, including areas of normal and infarcted tissue, with 5A reflecting the results realized when utilizing the self-calibrating method of the present invention and 5B providing the results obtained when utilizing a non-self-calibrated method. Recall that all prior art, such as that found in the aforementioned Miwa Patent, is non-self-calibrated. Since there is a great deal of variability in absorption, absolute reflectance and acoustic impedance between normal and infarcted heart tissue, and the resulting variations in returned ultrasound signals are encountered between adjacent scan regions, the lack of calibration results in grossly inexact diagnostic results as seen in FIG. 5B. The results in FIG. 5A were obtained by applying the steps in FIG. 3 to in vitro samples of heart tissue consisting of both normal and infarcted regions. The results in FIG. 5B were obtained by applying all of the steps in FIG. 3 except for the step 105 self-calibration. The self-calibration step was omitted in this case; that is, the separate power spectra from separate sites (30) within a region of interest (16), computed at 104, were averaged to form an average power spectrum for the region. Otherwise, the same input data and steps were used to generate both 5A and 5B. The results of FIGS. 5A and 5B can be summarized as follows.

| | c/a ratio (relative energy in high frequency bands)/(relative energy in low frequency bands) | | | |
|---|---|---|---|---|
| | Normal | | Infarct | |
| | mean ± sd | maximum | minimum | mean ± sd |
| 5A (self-calibrated method) | 0.28 ± 0.23 | 0.71 | 1.69 | 1.83 ± 0.10 |
| 5B (non-self-calibrated method) | 0.25 ± 0.22 | 0.63 | 0.03 | 0.26 ± 0.22 |

The self-calibrated method yields a clear separation between normal and infarcted tissue, and thus a range of possible clear diagnostic cut points. The energy ratios in the non-self-calibrated method are almost indistinguishable and of little, if any, diagnostic significance.

The high c/a ratio in infarcted heart tissue in FIG. 5A corresponds to a very low density of scatterers on the low frequency spatial scale; compared with the density on the high frequency scale.

The spatial frequency $f_{space}$ in cycles per centimeter associated with a frequency component $f_{time}$ in the amplitude modulation of the received waveform is inversely related to a spatial scale of scatterers or variations in density; the scale is given by $$1/f_{space} = (v/2) 1/f_{time} (\text{cm})$$

where v is the velocity of sound in cm/microsecond, and $f_{time}$ is the frequency of the amplitude modulation in MHz $$= 0.077 \times 2^n/\text{fs(cm)}$$

where f is the Fourier frequency (index of Fourier component) in cycles per sampling window of $2^n = k_{max}$ points per waveform, and s is the sampling rate in MHz.

Our "low frequency" band, comprising Fourier frequencies f from 5 to 20 cycles per window of 256 points ($2^n = 256$, or $n=8$), at a sampling rate of 50 MHz thus corresponds to spatial scales of 0.020 cm (for f=20) to 0.079 cm (for f=5), that is, approximately 200 to 800 microns.

In this manner, it is clear that more than a broad classification of normality or abnormality can be realized for smaller defined regions of interest. Examples of the specific diagnoses which can be made include the following:

essentially non-intrusive diagnosis of heart muscle disease including a determination of whether the damaged tissue can be repaired or not;

differentiation between plaque and thrombus in coronary arteries during angioplasty;

differentiation between malignant and benign tumors; and diagnosis of infiltrative versus inflammatory disease.

While the details of the present invention have been described with specific reference to a preferred embodiment and in the context of specific characterization of heart tissue, it is apparent that variations and applications may be made without departing from the spirit and scope of the inventive concept as defined by the appended claims.

What is claimed is:

1. A method for classifying tissue in a region of interest in a body comprising the steps of:

transmitting pulses of ultrasound energy into said body;

receiving pulses of returned ultrasound energy for said region of interest in said body;

digitizing said pulses of returned energy;

demodulating said pulses of returned energy by full-wave rectification to obtain the amplitude modulation in said digitized pulses of returned energy;

computing the power spectrum by performing a Fast Fourier Transform on said rectified digitized pulses of returned energy;

determining the Fourier energy in each of a plurality of selected Fourier frequency bands of the power spectrum of said digitized pulses;

selectively comparing the Fourier energies in said selected Fourier frequency bands to obtain at least one energy comparison; and correlating said at least one energy comparison to at least one tissue classification.

2. The method of claim 1 wherein said selectively comparing comprises obtaining ratios among energies in said selected frequency bands.

3. The method of claim 1 further comprising the step of storing said digitized pulses prior to said determining.

4. The method of claim 3 further comprising averaging said stored digitized pulses prior to said determining.

5. The method of claim 1 wherein said selectively comparing comprises obtaining at least one numerical value representing said relative amount of energy.

6. The method of claim 5 further comprising the steps of:

comparing said at least one numerical value to at least one table of known numerical classification values of normalized data; and classifying tissue in said region of interest based upon said comparing.

7. Apparatus for classifying tissue in a region of interest comprising:

means for generating ultrasound pulses;

transducer means for applying said ultrasound pulses to said region of interest and receiving returned ultrasound pulses from said body;

means for digitizing said returned ultrasound pulses;

means for demodulating said returned ultrasound pulses by full-wave rectification to obtain the amplitude modulation in said digitized returned ultrasound pulses;

computing means for computing the power spectrum by Fast Fourier Transform on said rectified digitized pulses;

means adapted to determine the Fourier energy in each of a plurality of selected Fourier frequency bands in the power spectrum of said digitized returned ultrasound pulses;

means for selectively comparing Fourier energies for said selected Fourier frequency bands of said power spectrum and obtaining at least one energy comparison; and correlating means for correlating said at least one energy comparison to at least one tissue classification.

8. The apparatus of claim 7 wherein said means for selectively comparing comprises means for obtaining ratios among energies in said selected frequency bands.

9. The apparatus of claim 7 further comprising storage means connected for storage of said digitized pulses.

10. The apparatus of claim 9 further comprising averaging means for averaging said stored digitized pulses.

11. The apparatus of claim 7 wherein said means for selectively comparing energy in each of a plurality of selected frequency bands comprises means for assigning at least one numerical value representing said relative amounts of energy.

12. The apparatus of claim 11 further comprising table storage means and wherein said means for correlating comprises means for comparing said at least one numerical value representing said relative amounts of energy to at least one stored table of known numerical classification values from normalized data.

13. A method for classifying tissue in a region of interest in a body comprising the steps of:

transmitting pulses of ultrasound energy into said body;

receiving pulses of returned ultrasound energy for said region of interest in said body;

digitizing said pulses of returned energy;

demodulating said pulses of returned energy to obtain the amplitude modulation in said digitized pulses of returned energy;

computing the power spectrum by performing a Fast Fourier Transform on said demodulated digitized pulses of returned energy;

determining the Fourier energy in each of a plurality of selected Fourier frequency bands of the power spectrum of said digitized pulses;

selectively comparing the Fourier energies for said selected Fourier frequency bands to obtain at least one energy comparison; and correlating said at least one energy comparison to at least one tissue classification.

14. Apparatus for classifying tissue in a region of interest comprising:

means for generating ultrasound pulses;

transducer means for applying said ultrasound pulses to said region of interest and receiving returned ultrasound pulses from said body;

means for digitizing said returned ultrasound pulses;

means for demodulating said returned ultrasound pulses to obtain the amplitude modulation in said digitized returned ultrasound pulses;

computing means for computing the power spectrum by Fast Fourier Transform on said modulated digitized pulses;

means adapted to determine the Fourier energy in each of a plurality of selected Fourier frequency bands in the power spectrum of said digitized returned ultrasound pulses;

means for selectively comparing Fourier energies for each of a plurality of selected Fourier frequency bands of said power spectrum and obtaining at least one energy comparison; and correlating means for correlating said at least one energy comparison to at least one tissue classification.

* * * * *